United States Patent
Li et al.

(10) Patent No.: US 10,132,891 B2
(45) Date of Patent: Nov. 20, 2018

(54) SYSTEM AND METHOD FOR ATTENUATION CORRECTION OF A SURFACE COIL IN A PET-MRI SYSTEM

(71) Applicant: GENERAL ELECTRIC COMPANY, Schenectady, NY (US)

(72) Inventors: Jiaqi Li, Brookfield, WI (US); Andrew Byshenk, Waukesha, WI (US); Chinmoy Goswami, Waukesha, WI (US); Tongzhou Wang, Beijing (CN)

(73) Assignee: General Electric Company, Schenectady, NY (US)

( * ) Notice: Subject to any disclaimer, the term of this patent is extended or adjusted under 35 U.S.C. 154(b) by 243 days.

(21) Appl. No.: 15/267,613

(22) Filed: Sep. 16, 2016

(65) Prior Publication Data

US 2018/0081014 A1    Mar. 22, 2018

(51) Int. Cl.
| | |
|---|---|
| *G01V 3/00* | (2006.01) |
| *G01R 33/48* | (2006.01) |
| *A61B 6/03* | (2006.01) |
| *A61B 6/00* | (2006.01) |
| *G01R 33/341* | (2006.01) |

(52) U.S. Cl.
CPC ........... *G01R 33/481* (2013.01); *A61B 6/037* (2013.01); *A61B 6/4417* (2013.01); *A61B 6/5258* (2013.01); *G01R 33/341* (2013.01)

(58) Field of Classification Search
USPC ........................................................ 324/309
See application file for complete search history.

(56) References Cited

U.S. PATENT DOCUMENTS

| | | | | |
|---|---|---|---|---|
| 9,430,717 | B2* | 8/2016 | Denissen | G06K 9/6214 |
| 9,857,443 | B2* | 1/2018 | Tadic | G01R 33/387 |
| 2010/0113959 | A1* | 5/2010 | Pascual-Leone | A61N 2/006 |
| | | | | 600/544 |
| 2011/0066026 | A1 | 3/2011 | Roeck et al. | |
| 2014/0155737 | A1* | 6/2014 | Manzke | A61B 6/032 |
| | | | | 600/417 |
| 2014/0187910 | A1 | 7/2014 | Culver et al. | |
| 2014/0266198 | A1* | 9/2014 | Tadic | G01R 33/387 |
| | | | | 324/309 |
| 2015/0238275 | A1* | 8/2015 | Kung | A61B 5/1073 |
| | | | | 600/424 |
| 2016/0242854 | A1* | 8/2016 | Grass | A61B 6/5252 |

* cited by examiner

*Primary Examiner* — Rodney Fuller
(74) *Attorney, Agent, or Firm* — Grogan, Tuccillo & Vanderleeden, LLP

(57) ABSTRACT

A PET-MRI system for imaging an object is provided. The PET-MRI system includes a magnetic resonance imaging sub-system, a positron emission tomography sub-system, an optical sensor, and a data processing controller. The magnetic resonance imaging sub-system includes a surface coil that acquires magnetic resonance signals from the object. The positron emission tomography sub-system acquires PET emissions from the object. The optical sensor detects at least one of a spatial location and a shape of the surface coil. The data processing controller communicates with the magnetic resonance imaging sub-system, the positron emission tomography sub-system, and the optical sensor, and utilizes at least one of the detected spatial location and the detected shape of the surface coil to correct the acquired PET emissions for attenuation.

20 Claims, 5 Drawing Sheets

SYSTEM AND METHOD FOR ATTENUATION CORRECTION OF A SURFACE COIL IN A PET-MRI SYSTEM

BACKGROUND

Technical Field

Embodiments of the invention relate generally to positron emission tomography ("PET") and magnetic resonance imaging ("MRI" or "MR imaging"), and more specifically, to a system and method for attenuation correction of a surface coil in a combined PET-MRI system.

Discussion of Art

PET imaging involves the creation of tomographic images of positron emitting radionuclides in a subject of interest. A radionuclide-labeled agent is administered to a subject positioned within a detector ring. As the radionuclides decay, positively charged electrons known as "positrons" are emitted therefrom. As these positrons travel through the tissues of the subject, they lose kinetic energy and ultimately collide with an electron, resulting in mutual annihilation. The positron annihilation results in a pair of oppositely-directed gamma rays being emitted at approximately 511 keV, which are subsequently detected by scintillators in the detector ring. When struck by a gamma ray, each scintillator illuminates, activating a photovoltaic component, such as a photodiode.

The signals from the photovoltaics are processed as incidences of gamma rays. When two gamma rays strike oppositely positioned scintillators at approximately the same time, a coincidence is registered. Data sorting units process the coincidences to determine true coincidence events and to sort out data representing dead times and single gamma ray detections. The coincidence events are binned and integrated to form frames of PET data which may be reconstructed into images depicting the distribution of the radionuclide-labeled agent and/or metabolites thereof in the subject.

MRI obtains digitized visual images representing the internal structure of objects having substantial populations of atomic nuclei that are susceptible to nuclear magnetic resonance ("NMR"). Many MRI systems use magnet assemblies that house superconductive magnets to impose a strong main magnetic field on the nuclei in the patient/object to be imaged within a target volume (hereinafter also referred to as the "imaging bore" and/or simply "bore"). The nuclei are excited by a radio frequency ("RF") signal typically transmitted via an RF coil at characteristics NMR (Larmor) frequencies. By spatially disturbing localized magnetic fields surrounding the object within the imaging bore, and analyzing the resulting RF responses (also referred to herein as "MR signals") from the nuclei as the excited protons relax back to their lower energy normal state, a map or image of these nuclei responses as a function of their spatial location is generated and displayed. An image of the nuclei responses provides a non-invasive view of an object's internal structure.

In many MRI systems, the best excitation field homogeneity is typically obtained by using a whole-body volume RF coil for transmission. The whole-body transmit coil is often the largest RF coil in such MRI systems. A large RF coil, however, produces lower signal-to-noise ratio ("SNR") if it is also used to receive the RF responses, mainly because such RF coils are often at great distances from the signal-generating tissues being imaged. Because a high SNR is usually desirable in MRI, "surface coils" are commonly employed for reception of the RF responses to enhance the SNR from a particular volume-of-interest. Generally, surface coils are relatively small and are constructed to receive the RF responses from a localized portion of the patient, e.g., different surface coils may be employed for imaging the head, neck, legs, arms, and/or various internal organs.

In a combined PET-MRI system, however, surface coils can potentially distort, i.e., attenuate, the emitted gamma rays prior to detection by the scintillators in the detector ring. Accordingly, many PET-MRI systems rely on attenuation correction algorithms to compensate for the distortion caused by surface coils. Such algorithms, however, often require that the shape, location, and material density of the surface coils be known with a high level of precision. As a result, many PET-MRI systems are limited to using so called non-floating "rigid" surface coils, which are typically non-flexible and mounted/fixed to a known stationary location.

Many MRI systems, however, utilize floating surface coils, which generally produce greater SNR than rigid surface coils as they are typically placed on a patient's body and are thus closer to the imaged tissue. Indeed, floating surface coils are typically supported by a patient's body, and therefore often move in relation to a patient's movement. As a result, the location of such coils is neither fixed nor known with great precision. Many floating surface coils are flexible, i.e., non-rigid, as well such that the coil shape may also not be known with great precision.

What is needed, therefore, is an improved system and method for attenuation correction of a surface coil that provides for the use of floating surface coils and/or flexible coils in a PET-MRI system.

BRIEF DESCRIPTION

In an embodiment, a PET-MRI system for imaging an object is provided. The PET-MRI system includes a magnetic resonance imaging sub-system, a positron emission tomography sub-system, an optical sensor, and a data processing controller. The magnetic resonance imaging sub-system includes a surface coil that acquires magnetic resonance signals from the object. The positron emission tomography sub-system acquires PET emissions from the object. The optical sensor detects at least one of a spatial location and a shape of the surface coil. The data processing controller communicates with the magnetic resonance imaging sub-system, the positron emission tomography sub-system, and the optical sensor, and utilizes at least one of the detected spatial location and the detected shape of the surface coil to correct the acquired PET emissions for attenuation.

In another embodiment, a method for performing PET-MR imaging of an object is provided. The method includes: detecting at least one of a spatial location and a shape of a surface coil via an optical sensor; acquiring PET emissions from the object via a positron emission tomography sub-system; and correcting the acquired PET emissions for attenuation utilizing at least one of the detected spatial location and the detected shape of the surface coil via a data processing controller in communication with the optical sensor and the positron emission tomography sub-system.

In yet another embodiment, a surface coil for a PET-MRI system that images an object is provided. The surface coil includes a body having an exterior surface, and a fiber optic cable. The surface coil acquires magnetic resonance signals from the object, and the fiber optic cable provides for detection of at least one of a spatial location and a shape of the surface coil.

DRAWINGS

The present invention will be better understood from reading the following description of non-limiting embodiments, with reference to the attached drawings, wherein below:

Figure 1:
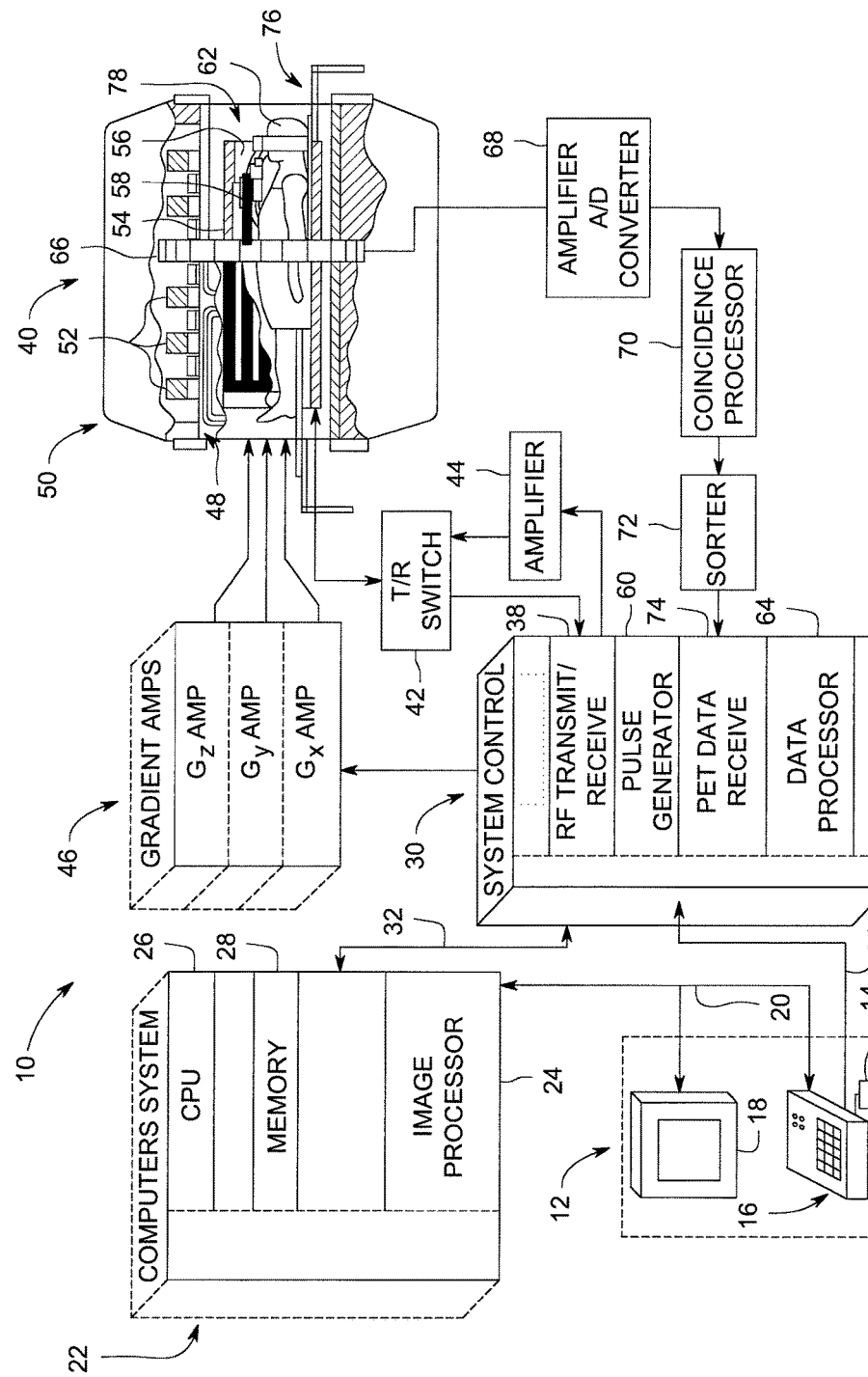
FIG. 1 is a schematic block diagram of a PET-MRI system that includes a magnet assembly in accordance with an embodiment of the present invention.
Figure 4:
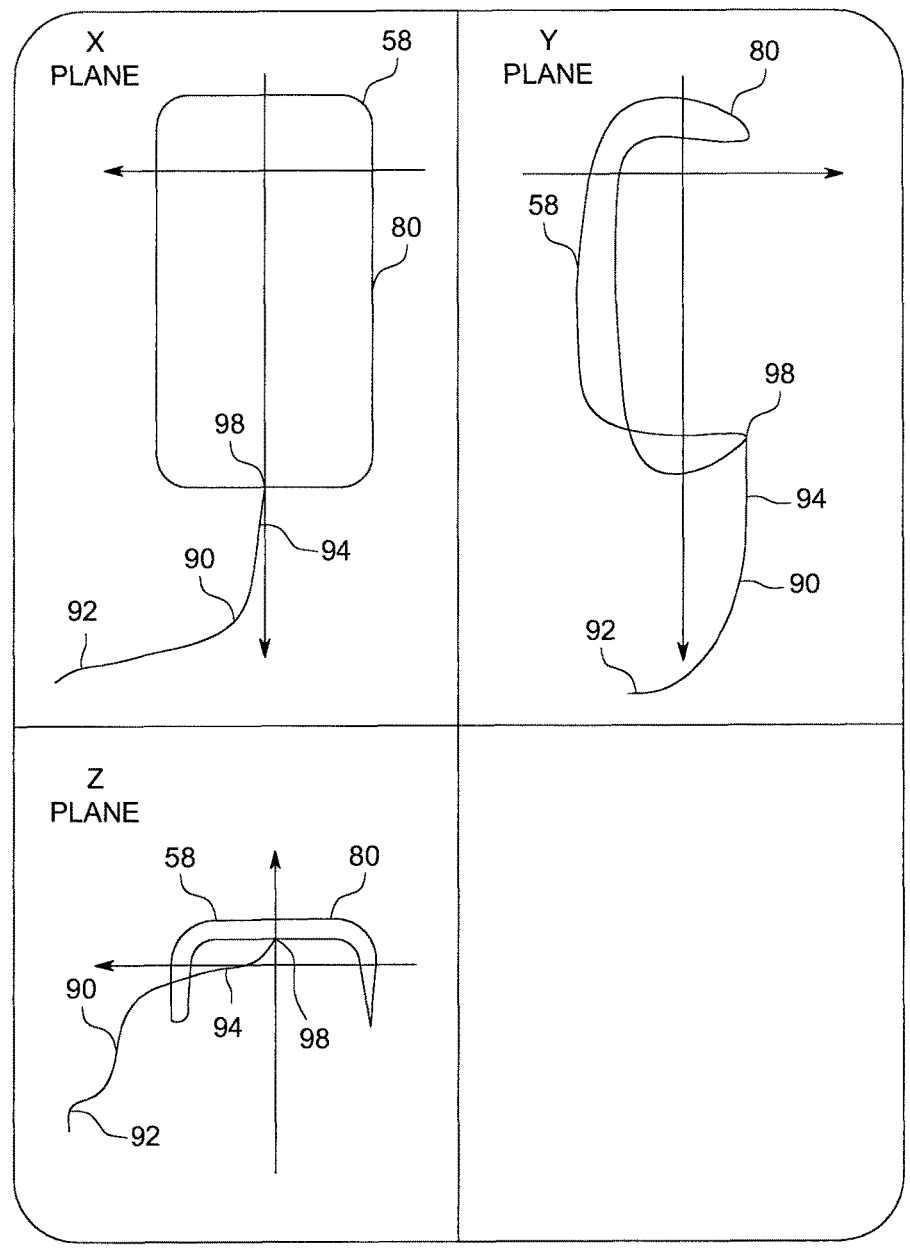
Figure 5:
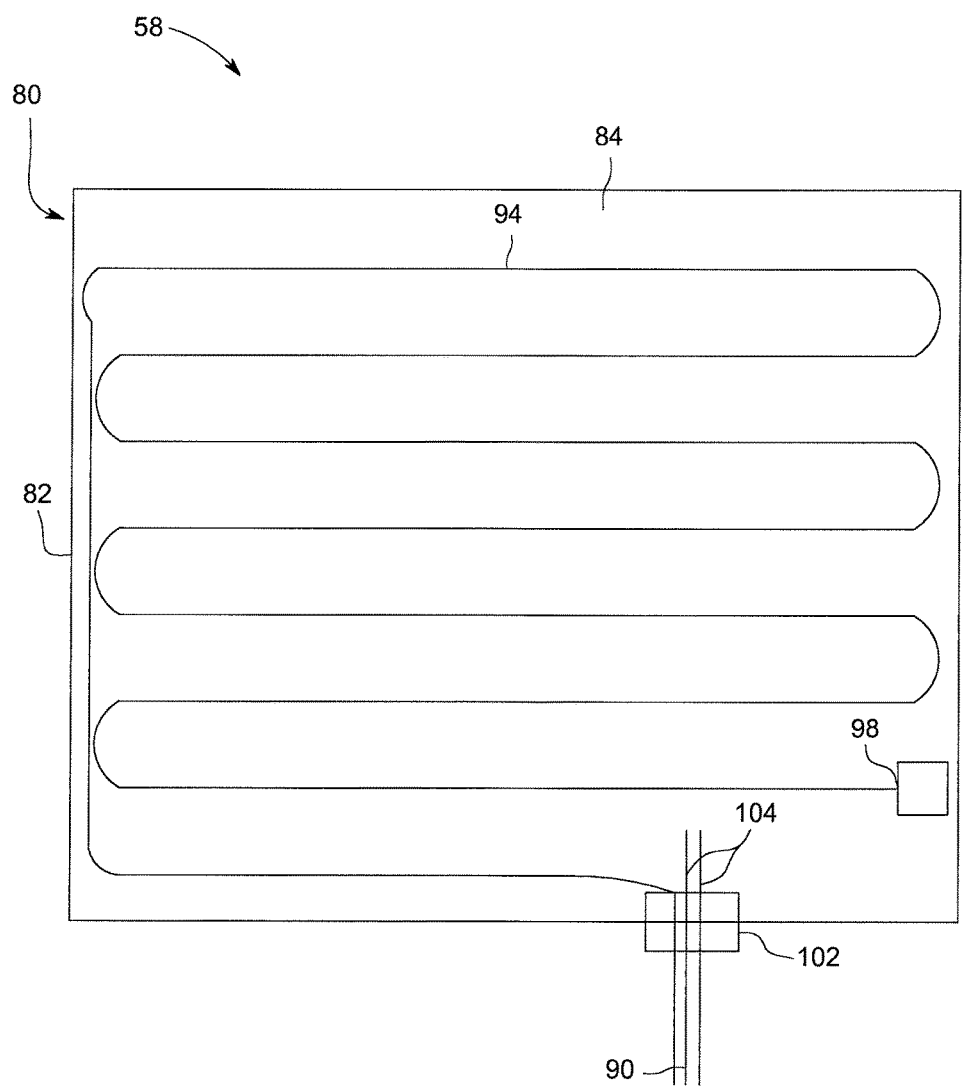

FIG. 4 is a graphical diagram depicting x, y, and z planar projections of a surface coil and a fiber optic cable of the PET-MRI system of FIG. 1 in accordance with an embodiment of the present invention; and FIG. 5 is a diagram of a surface coil of the PET-MRI system of FIG. 1, wherein the surface coil includes an integrated fiber optic cable in accordance with an embodiment of the present invention.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. The term "real-time," as used herein, means a level of processing responsiveness that a user senses as sufficiently immediate or that enables the processor to keep up with an external process. As also used herein, the term "spatial location" means the location and/or orientation of an object in two-dimensional and/or three-dimensional space. As used herein, "electrically coupled", "electrically connected", "electrical communication", and "communication" mean that the referenced elements are directly or indirectly connected such that an electrical current, or other communication medium, may flow from one to the other. The connection may include a direct conductive connection, i.e., without an intervening capacitive, inductive or active element, an inductive connection, a capacitive connection, and/or any other suitable electrical connection. Intervening components may be present. As further used herein, the term "attenuation correction" means a process and/or algorithm that corrects/accounts for the distortion in PET imaging resulting from the loss of detection events due to absorption and/or scattering of gamma rays produced from the decay of a radionuclide-labeled agent that has been injected into an object to be imaged.

Additionally, while the embodiments disclosed herein are described with respect to a hybrid PET-MRI system, it is to be understood that embodiments of the present invention may be applicable to other imaging systems, e.g., SPECT/ MR, and/or other similar imaging systems. Further, as will be appreciated, embodiments of the present invention related imaging systems may be used to analyze animal tissue, and other materials generally, and are not limited to human tissue.

Referring now to FIG. 1, the major components of a hybrid PET-MRI system 10 that incorporates embodiments of the present invention are shown. As will be appreciated and described below, the PET-MRI system 10 combines both a PET sub-system and an MRI sub-system. The operation of the system 10 may be controlled from an operator console 12 which includes a keyboard or other input device 14, a control panel 16, and a display screen 18. The console 12 communicates through a link 20 with a separate computer system 22 that enables an operator to control the production and display of images on the display screen 18. The computer system 22 includes a number of modules, such as an image processor module 24, a CPU module 26, and a memory module 28. The computer system 22 may also be connected to permanent or back-up memory storage, a network, or may communicate with a separate system controller 30 through link 32. The input device 14 can include a mouse, keyboard, track ball, touch activated screen, light wand, or any similar or equivalent input device, and may be used for interactive geometry prescription.

The system controller 30 includes a set of modules in communication with one another and connected to the operator console 12 through link 34. It is through link 32 that the system controller 30 receives commands to indicate the scan sequence or sequences that are to be performed. For MRI data acquisition, an RF transmit/receive module 38 commands the scanner 40 to carry out the desired scan sequence, by sending instructions, commands, and/or requests describing the timing, strength and shape of the RF pulses and pulse sequences to be produced, to correspond to the timing and length of the data acquisition window. In this regard, a transmit/receive switch 42 controls the flow of data via amplifier 44 to scanner 40 from RF transmit module 38, and from scanner 40 to RF receive module 38. The system controller 30 also connects to a gradient amplifier sub-system 46, having amplifiers $G_x$, $G_y$, and $G_z$, to indicate the timing and shape of the gradient pulses that are produced during the scan.

The gradient waveform instructions produced by system controller 30 are sent to the gradient amplifier sub-system 46 which may be external of the scanner 40 or of the system controller 30, or may be integrated therein. Each gradient amplifier, $G_x$, $G_y$, and $G_z$, excites a corresponding physical gradient coil in a gradient coil assembly generally designated 48 to produce the magnetic field gradients used for spatially encoding acquired signals. The gradient coil assembly 48 forms part of a magnet assembly 50 which includes a polarizing magnet 52 and an RF coil assembly 54. Alternatively, the gradient coils of gradient coil assembly 48 may be independent of the magnet assembly 50. In embodiments, the RF coil assembly 54 may include a whole-body RF transmit coil 56. As will be appreciated, coil 56 of the RF coil assembly 54 may be configured for transmitting RF pulses while a separate surface coil 58 is configured to receive RF signals. A pulse generator 60 may be integrated into the system controller 30 as shown, or may be integrated into the MRI scanner 40, to produce pulse sequences or pulse sequence signals for the gradient amplifiers 46 and/or the RF coil assembly 54. In addition, pulse generator 60 may generate PET data blanking signals synchronously with the production of the pulse sequences. These blanking signals may be generated on separate logic lines for subsequent data processing. The MR signals resulting from the excitation pulses, emitted by the excited nuclei in a patient/subject/imaged object 62, may be sensed by surface coil 58 and then transmitted to the RF transmit/receive module 38 via T/R switch 42. The MR signals are demodulated, filtered, and digitized in a data processing controller/processor 64 of the system controller 30.

An MRI scan is complete when one or more sets of raw k-space data has been acquired in the data processing controller 64. This raw k-space data is reconstructed in data processing controller 64 which operates to transform the data (through Fourier or other techniques) into image data. This image data is conveyed through link 32 to the computer system 22 where it is stored in the memory module 28. Alternatively, in some embodiments, computer system 22 may assume the image data reconstruction and other functions of data processing controller 64. In response to commands received from the operator console 12, the image data stored in memory module 28 may be archived in long term storage or may be further processed by the image processor 24 or CPU 26, conveyed to the operator console 12, and presented on the display 18.

In combined PET-MRI systems, PET data may be acquired simultaneously with the MRI data acquisition described above. Thus, the scanner 40 also includes a positron emission detector array or ring 66 configured to detect gamma rays from positron annihilations emitted from the imaged subject 62. The detector ring 66 preferably includes a plurality of scintillators and photovoltaics arranged about a gantry. As will be appreciated, however, in embodiments, the detector array 66 may be of any suitable construction for acquiring PET data. In addition, the scintillator, photovoltaics, and other electronics of the detector ring 66 need not be shielded from the magnetic fields and/or RF fields applied by the polarizing magnet 52 and whole-body RF transmit coil 56. However, it is contemplated that embodiments of the present invention may include such shielding as known in the art, or may be combined with various other shielding techniques.

Gamma ray incidences detected by the detector ring 66 are transformed, by the photovoltaics of the detector ring 66, into electrical signals which are conditioned by a series of front end electronics 68. These conditioning circuits 68 may include various amplifiers, filters, and analog-to-digital converters. The digital signals outputted from the front end electronics 68 are then processed by a coincidence processor 70 to match gamma ray detections as potential coincidence events. When two gamma rays strike detectors approximately opposite one another, it is possible, absent the interactions of random noise and signal gamma ray detections, that a positron annihilation took place somewhere along the line between the detectors. Thus, the coincidences determined by coincidence processor 70 are sorted into true coincidence events and ultimately integrated by data sorter 72. The coincidence event data, or PET data, from sorter 72 is received by the system controller 30 at a PET data receive port 74 and stored in memory 28 for subsequent processing by the data processing controller 64. PET images may then be reconstructed by image processor 24 and combined with MR images to produce hybrid structural and metabolic or functional images. Conditioning circuits 68, coincidence processor 70, and sorter 72 may each be external of the scanner 40 or the system controller 30, or may be integrated therein.

Also included in PET-MR imaging system 10 is a patient support assembly/cradle 76 configured to support the patient/subject 62 within a bore 78 of the magnet assembly 50 during data acquisition. The patient cradle 76 enables movement of the patient 62 into various positions with respect to the magnet assembly 50, including a loading position outside the bore 78, and at least one imaging position, where at least a portion of the patient/subject 62 is positioned within an imaging volume (i.e., within the bore 78) when at the imaging position.

Figure 2:
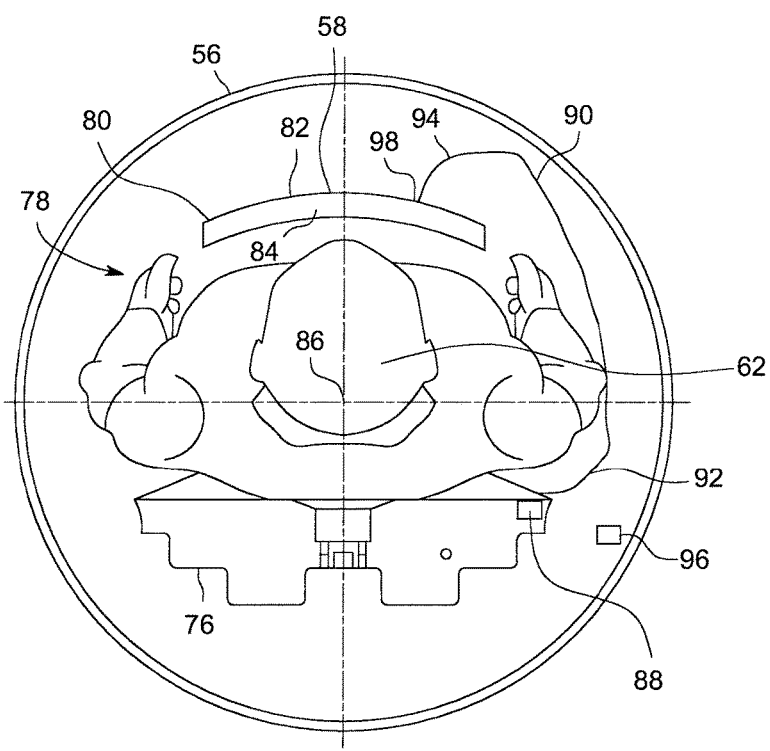
FIG. 2 is a perspective view of the magnet assembly of FIG. 1 in accordance with an embodiment of the present invention.
Figure 3:
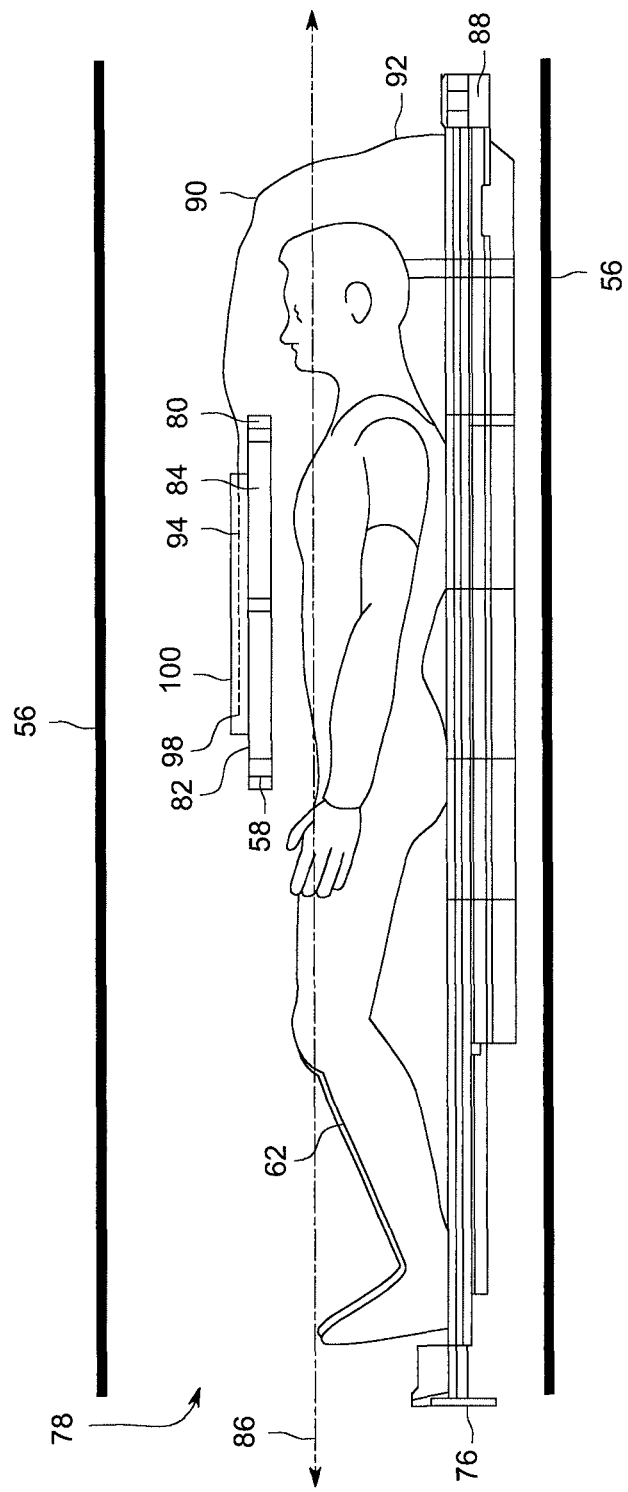
FIG. 3 is another perspective view of the magnet assembly of FIG. 1 in accordance with an embodiment of the present invention.

As illustrated in FIGS. 2 and 3, in embodiments, the surface coil 58 includes a body 80 having an exterior surface 82 that defines an interior volume 84, and is configured to rest and/or be supported by the patient 62, i.e, in embodiments, the surface coil 58 may be a floating surface coil. In such embodiments, the surface coil 58 is not fixed to a known stationary location. Accordingly, the surface coil 58 may move in response to movements by the patient 62 in relation to a center axis 86 of the bore 78. While the surface coil 58 depicted in FIGS. 2 and 3 is configured to cover the patient's 62 torso, it is to be appreciated that the surface coil 58 may be configured to cover other areas of the patient 62, e.g., the head, arms, lower torsos, legs, etc. Further, the surface coil 58 may be either rigid, i.e., non-flexible, and/or flexible, e.g., adjustably and/or naturally conforming to the shape of the patient 62.

As further shown in FIGS. 2 and 3, the PET-MRI system 10 may also include an optical sensor 88 configured to detect at least one of a spatial location and/or a shape of the floating surface coil 58. For example, in embodiments, the optical sensor 88 may include a fiber optic cable 90 and be configured to detect the location and/or the shape of the surface coil 58 by determining a shape of the fiber optic cable 90. The fiber optic cable 90 may be on the order of <1 mm and made from low density material. As will be understood, the optical sensor 88 may be configured to reconstruct the shape of the fiber optic cable 90 by accumulating the bending strain of various segments of the fiber optic cable by known means in the art. In other words, the optical sensor 88 can determine the shape of the fiber optic cable 90, to include bends, twists, and/or kinks, by analyzing the characteristics of the light traveling through the fiber optic cable 90 in real-time and/or near real-time, e.g. a resolution of 10 Hz, with a high level of precision, e.g., within 1 mm. In such embodiments, the fiber optic cable 90 may include a first end 92 and a second end 94, the first end 92 being connected/disposed at an anchor location and the second end 94 connected/disposed at the surface coil 58. As used herein, the term "anchor location" refers to a location having a position that can be determined with respect to the detector ring 66 to a relatively high level of precision without the use of the optical sensor 88. For example, in embodiments, the anchor location may be a coil port 96 on a fixed structure/component of the PET-MRI system 10, and/or a location on the patient cradle 76.

Turning now to FIG. 4, x, y, and z planar projections of the surface coil 58 and fiber optic cable 90 are shown. As will be appreciated, the point at which the second end 94 of the fiber optic cable 90 contacts the surface coil 58 may serve as a coordination center point 98. As will be appreciated, the coordination center point 98 is a known location on and/or within the surface coil 58 from which the location of the body 80 can be calculated and/or interpolated from based on known characteristics of the surface coil 58, e.g., approximate shape, length, height, width, depth, etc. Thus, since the location of the first end 92 is at a known anchor location, e.g., a point on the patient cradle (76 in FIGS. 2 and 3) and/or a coil port (96 in FIG. 2), the location of the second end 94 can be calculated in three-dimensional space based on the determined shape of the fiber optic cable 90. Therefore, the location of the coordination center point 98 can then be determined in three-dimensional space from the calculated location of the second end 94. Once the location of the coordination center point 98 has been calculated/determined, the three-dimensional location/orientation of the surface coil 58 can then be found. Accordingly, as will be further appreciated, in embodiments, the shape of the surface coil 58 can be acquired in six (6) DOF, i.e., three (3) translation and three (3) rotations, via the fiber optic cable 90.

Referring back to FIGS. 2 and 3, as is to be further appreciated, in embodiments, the aforementioned calculations may be performed by the data processing controller 64 and/or another suitable processor located in a component of the PET-MRI system 10. In such embodiments, the optical sensor 88 may be located on/within a stationary component of the PET-MRI system 10, such as the magnet assembly 50 and/or patient cradle 76, with the first end 92 of the fiber optic cable 90 connected to the optical sensor 88. The optical sensor 88 may then serve as a transducer that converts optical measurements of the light within the fiber optic cable 90 into analogue and/or digital signals that are then communicated to an appropriate processor, e.g. the data processing controller 64. The data processing controller 64 may then use the received surface coil 58 shape and/or location information to perform attenuation correction of the acquired PET emissions.

As will also be understood, in embodiments, the second end 94 of the fiber optic cable 90 may be disposed/connected to the exterior surface 82 of the surface coil 58. In particular, as shown in FIG. 2, in embodiments, the second end 94 of the fiber optic cable 90 may be connected/disposed at a single point on the surface coil 58. Additionally, and as shown in FIG. 3, in other embodiments, the second end 94 of the fiber optic cable 90 may be incorporated into a sensor mat 100 that is configured to be disposed/placed over the exterior surface 82 of the surface coil 58. The sensor mat 100 may be made of plastic and/or flexible fabric such that the sensor mat 100 conforms to the shape of the surface coil 58 when placed over the surface coil 58. In such embodiments, the fiber optic cable 90 may span/cover an area larger than a single point when within the sensor mat 100, i.e., the sensor mat 100 is configured to support the fiber optic cable 90 such that substantial portions of the fiber optic cable 90 can conform to the shape of the surface coil 58 when the sensor mat 100 is placed over the surface coil 58. Accordingly, and as will be appreciated, having substantial portions of the fiber optic cable 90 conform to the shape of the surface coil 58 enables the shape of the surface coil 58 to be calculated/determined/detected based upon the determined shape of the fiber optic cable 90.

Referring now to FIG. 5, the surface coil 58 is depicted wherein part of the exterior surface 82 is removed from view such that the interior volume 84 is visible. As shown in FIG. 5, in embodiments, the fiber optic cable 90 may be incorporated/integrated into the surface coil 58. In such embodiments, the surface coil 58 may include a common port 102 through which passes both the fiber optic cable 90 and communication cables 104, that allow the surface coil 58 to communicate the received RF responses/magnetic resonance signals to the system controller 30 and/or image processor 24. As further illustrated in FIG. 5, similar to embodiments in which the fiber optic cable 90 is incorporated into the sensor mat 100 (shown in FIG. 3), a substantial portion of the fiber optic cable 90 may be incorporated into the sensor coil 58 so as to enable the detection/calculation of the shape of the sensor coil 58.

Finally, it is also to be understood that the PET-MRI system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the PET-MRI system 10 may include at least one processor (e.g., 24, 26, and 64 in FIG. 1), and system memory/data storage structures (e.g., 28 in FIG. 1), which may include random access memory (RAM) and read-only memory (ROM). The at least one processor of the PET-MRI system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that provides for the calculation/detection/determination of the shape of the fiber optic cable 90 and/or the surface coil 58, as well as for the attenuation correction of the received PET emissions, may be read into a main memory of the at least one processor from a computer-readable medium. The term "computer-readable medium", as used herein, refers to any medium that provides or participates in providing instructions to the at least one processor of the PET-MRI system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment a PET-MRI system for imaging an object is provided. The PET-MRI system includes a magnetic resonance imaging sub-system, a positron emission tomography sub-system, an optical sensor, and a data processing controller. The magnetic resonance imaging sub-system includes a surface coil that acquires magnetic resonance signals from the object. The positron emission tomography sub-system acquires PET emissions from the object. The optical sensor detects at least one of a spatial location and a shape of the surface coil. The data processing controller communicates with the magnetic resonance imaging sub-system, the positron emission tomography sub-system, and the optical sensor, and utilizes at least one of the detected spatial location and the detected shape of the surface coil to correct the acquired PET emissions for attenuation. In certain embodiments, the optical sensor includes a fiber optic cable and detects at least one of the spatial location and the shape of the surface coil by determining a shape of the fiber optic cable. In certain embodiments, the fiber optic cable has a first end disposed at an anchor location and a second end disposed at the surface coil. In certain embodiments, the anchor location is at least one of a coil port and a patient cradle. In certain embodiments, the fiber optic cable is disposed on an exterior surface of the surface coil. In certain embodiments, the fiber optic cable is incorporated into a sensor mat that is disposed on an exterior surface of the surface coil. In certain embodiments, the fiber optic cable is integrated into the surface coil. In certain embodiments, the surface coil includes a common port through which passes both the fiber optic cable and communication cables that allow the surface coil to communicate the received magnetic resonance signals to the data processing controller.

Other embodiments provide for a method for performing PET-MR imaging of an object. The method includes: detecting at least one of a spatial location and a shape of a surface coil via an optical sensor; acquiring PET emissions from the object via a positron emission tomography sub-system; and correcting the acquired PET emissions for attenuation utilizing at least one of the detected spatial location and the detected shape of the surface coil via a data processing controller in communication with the optical sensor and the positron emission tomography sub-system. In certain embodiments, the optical sensor includes a fiber optic cable. In such embodiments, detecting at least one of a spatial location and a shape of a surface coil via an optical sensor includes determining the shape of the fiber optic cable. In certain embodiments, the fiber optic cable has a first end disposed at an anchor location and a second end disposed at the surface coil. In certain embodiments, the anchor location is at least one of a coil port and a patient cradle. In certain embodiments, the method further includes placing the fiber optic cable on an exterior surface of the surface coil. In certain embodiments, the fiber optic cable is incorporated into a sensor mat, and the method further includes placing the sensor mat on an exterior surface of the surface coil. In certain embodiments, the fiber optic cable is incorporated into the surface coil.

Yet still other embodiments provide for a surface coil for a PET-MRI system that images an object. The surface coil includes a body having an exterior surface, and a fiber optic cable. The surface coil acquires magnetic resonance signals from the object, and the fiber optic cable provides for detection of at least one of a spatial location and a shape of the surface coil. In certain embodiments, the fiber optic cable is disposed on the exterior surface of the body. In certain embodiments, the fiber optic cable is incorporated into a sensor mat that is disposed on the exterior surface of the body. In certain embodiments, the optical sensor is integrated into the body. In certain embodiments, the body further includes a common port through which passes both the fiber optic cable and communication cables that allow the surface coil to communicate received magnetic resonance signals to a data processing controller of the PET-MRI system.

Additionally, in embodiments, the optical sensor 88 and fiber optic cable 90 may be applied to determine the location of additional objects besides the surface coil 58.

Accordingly, by utilizing an optical sensor 88 to determine the location of a surface coil 58, some embodiments of the invention provide for attenuation correction of PET emissions that accounts for a floating surface coil within a PET-MRI system 10. Thus, as floating surface coils provide for higher SNR than traditional fixed rigid surface coils, such embodiments provide for a significant increase in the quality and/or resolution of PET-MRI imaging. Moreover, because the optical sensor 88 relies on light as the sensing medium, some embodiments of the invention provide for the above mentioned increase in SNR without affecting the magnetic fields and/or RF signals of the MRI components of the combined PET-MRI system 10. Accordingly, some embodiments of the PET-MRI system 10 provide for as much as a 4-6% increase in geometric accuracy over traditional PET-MRIs without impacting the MR imaging.

Additionally, because the optical sensor 88 determines the location of the surface coil 58 via the fiber optic cable 90, some embodiments of the invention provide for the aforementioned attenuation correction without the need for certain procedures, e.g., patient breath holds, that increase the scan time of the PET-MRI system 10.

Further, some embodiments having surface coils 58 with integrated fiber optic cables 90 provide for the ability to rapidly place and/or change out surface coils 58 for a given PET-MRI scan. Similarly, some embodiments that utilize a sensor mat 100 also provide for the ability to place and/or change out surface coils 58 for a given PET-MRI scan, which while taking slightly longer than embodiments having surface coils 58 with incorporated/integrated fiber optic cables 90, may be performed at a lower financial cost.

Further still, in some embodiments, the optical sensor 88 and fiber optic cable 90 are separate and distinct pieces of hardware apart from the polarizing magnet 52 and whole-body RF coil 56. Thus, such embodiments provide for independence from the polarizing magnet 52 and whole-body RF coil 56 which may improve reliability in performing attenuation correction of the acquired PET emissions.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A PET-MRI system for imaging an object comprising:
    a magnetic resonance imaging sub-system that includes a surface coil that acquires magnetic resonance signals from the object;
    a positron emission tomography sub-system that acquires PET emissions from the object;
    an optical sensor that detects at least one of a spatial location and a shape of the surface coil;
    a data processing controller that communicates with the magnetic resonance imaging sub-system, the positron emission tomography sub-system, and the optical sensor; and
    wherein the data processing controller utilizes at least one of the detected spatial location and the detected shape of the surface coil to correct the acquired PET emissions for attenuation.

2. The PET-MRI system of claim 1, wherein the optical sensor includes a fiber optic cable and detects at least one of the spatial location and the shape of the surface coil by determining a shape of the fiber optic cable.

3. The PET-MRI system of claim 2, wherein the fiber optic cable has a first end disposed at an anchor location and a second end disposed at the surface coil.

4. The PET-MRI system of claim 3, wherein the anchor location is at least one of a coil port and a patient cradle.

5. The PET-MRI system of claim 2, wherein the fiber optic cable is disposed on an exterior surface of the surface coil.

6. The PET-MRI system of claim 2, wherein the fiber optic cable is incorporated into a sensor mat that is disposed on an exterior surface of the surface coil.

7. The PET-MRI system of claim 2, wherein the fiber optic cable is integrated into the surface coil.

8. The PET-MRI system of claim 7, wherein the surface coil includes a common port through which passes both the fiber optic cable and communication cables that allow the surface coil to communicate the received magnetic resonance signals to the data processing controller.

9. A method for performing PET-MR imaging of an object, the method comprising:
    detecting at least one of a spatial location and a shape of a surface coil via an optical sensor;
    acquiring PET emissions from the object via a positron emission tomography sub-system; and
    correcting the acquired PET emissions for attenuation utilizing at least one of the detected spatial location and the detected shape of the surface coil via a data processing controller in communication with the optical sensor and the positron emission tomography sub-system.

10. The method of claim 9, wherein the optical sensor includes a fiber optic cable, and
    detecting at least one of a spatial location and a shape of a surface coil via an optical sensor comprises:
    determining the shape of the fiber optic cable.

11. The method of claim 10, wherein the fiber optic cable has a first end disposed at an anchor location and a second end disposed at the surface coil.

12. The method of claim 11, wherein the anchor location is at least one of a coil port and a patient cradle.

13. The method of claim 10 further comprising:
    placing the fiber optic cable on an exterior surface of the surface coil.

14. The method of claim 10, wherein the fiber optic cable is incorporated into a sensor mat, and the method further comprises:
    placing the sensor mat on an exterior surface of the surface coil.

15. The method of claim 10, wherein the fiber optic cable is incorporated into the surface coil.

16. A surface coil for a PET-MRI system that images an object, the surface coil comprising:
    a body having an exterior surface;
    a fiber optic cable; and
    wherein the surface coil acquires magnetic resonance signals from the object, and
    the fiber optic cable provides for detection of at least one of a spatial location and a shape of the surface coil.

17. The surface coil of claim 16, wherein the fiber optic cable is disposed on the exterior surface of the body.

18. The surface coil of claim 16, wherein the fiber optic cable is incorporated into a sensor mat that is disposed on the exterior surface of the body.

19. The surface coil of claim 16, wherein the optical sensor is integrated into the body.

20. The surface coil of claim 19, wherein the body further includes a common port through which passes both the fiber optic cable and communication cables that allow the surface coil to communicate received magnetic resonance signals to a data processing controller of the PET-MRI system.

* * * * *